(12) United States Patent
Noack et al.

(10) Patent No.: US 8,604,071 B2
(45) Date of Patent: Dec. 10, 2013

(54) METHOD FOR PRODUCING HYDROXYMETHYL DIPHENYLOXIRANES AND CORRESPONDING 1-AZOLYLMETHYL-1,2-DIPHENYLOXIRANES

(75) Inventors: Rainer Noack, Grossthiemig (DE); Clemens Palm, Dresden (DE); Carsten Groening, Mannheim (DE); Gunter Lipowsky, Ladenburg (DE)

(73) Assignee: BASF SE, Ludwigshafen (DE)

( * ) Notice: Subject to any disclaimer, the term of this patent is extended or adjusted under 35 U.S.C. 154(b) by 153 days.

(21) Appl. No.: 13/147,648

(22) PCT Filed: Feb. 4, 2010

(86) PCT No.: PCT/EP2010/051380
§ 371 (c)(1),
(2), (4) Date: Aug. 3, 2011

(87) PCT Pub. No.: WO2010/089353
PCT Pub. Date: Aug. 12, 2010

(65) Prior Publication Data
US 2011/0295019 A1    Dec. 1, 2011

(30) Foreign Application Priority Data
Feb. 5, 2009    (EP) .................................. 09152176

(51) Int. Cl.
*A61K 31/41*    (2006.01)
*A61K 31/415*    (2006.01)
*C07D 207/00*    (2006.01)
*C07D 249/00*    (2006.01)

(52) U.S. Cl.
USPC ........... 514/385; 540/25; 548/300.1; 549/202

(58) Field of Classification Search
USPC ........... 514/385; 540/25; 548/300.1; 549/202
See application file for complete search history.

(56) References Cited

U.S. PATENT DOCUMENTS

| 4,940,717 A | 7/1990 | Seele et al. |
| 5,017,594 A * | 5/1991 | Seele et al. ..................... 514/383 |
| 5,028,618 A | 7/1991 | Seele et al. |
| 5,057,531 A | 10/1991 | Seele et al. |
| 5,098,917 A * | 3/1992 | Seele et al. ..................... 514/333 |
| 5,132,318 A * | 7/1992 | Seele et al. ..................... 514/397 |
| 5,162,357 A | 11/1992 | Seele et al. |
| 5,194,444 A * | 3/1993 | Seele et al. ..................... 514/383 |
| 7,276,632 B2 | 10/2007 | Noack et al. |
| 7,745,658 B2 | 6/2010 | Lipowsky et al. |

FOREIGN PATENT DOCUMENTS

| EP | 0 330 132 | 8/1989 |
| EP | 0 332 073 | 9/1989 |
| EP | 0 334 035 | 9/1989 |
| EP | 0 352 673 | 1/1990 |
| EP | 0 352 675 | 1/1990 |
| EP | 0 421 125 | 4/1991 |
| WO | WO 2005/056498 | 6/2005 |

OTHER PUBLICATIONS

International Search Report prepared in International Application No. PCT/EP2010/051380, filed Feb. 4, 2010.
International Preliminary Report on Patentability from corresponding International Application No. PCT/EP2010/051380, filed Feb. 4, 2010.
Burger, T. et al., "Synthesis of Four $^{14}$C-Isotopomers of Epoxiconazole, a New Triazole Fungicide", Journal of Labelled Compounds and Radiopharmaceuticals, (1996), pp. 173-178, vol. 38. No. 2.
Madelung, W. et al, "a-Keto-aldehyde", Chem. Ber., (1932), pp. 931-941, vol. 65.
Ogata, M. et al., "Synthesis and oral anti-fungal activity of novel 1, 3-bis-(azolyl)-2-arylpropan-2-ols", Eur. J. Med. Chem., (1989), pp. 137-143, vol. 24.
Pfenninger, A., "Asymmetric Epoxidation of Allylic Alcohols: The Sharpless Epoxidation", Synthesis, (1986), pp. 89-116.
Wadsworth et al., "Synthetic Applications of Phosphoryl-Stabilized Anions", Org. Reactions, (1977), pp. 73-253, vol. 25.
Zimmerman, et al., "Overlap Control of Carbanionoid Reactions. I. Stereoselectivity in Alkaline Epoxidation", Journal of the American Chemical Society, (1959), pp. 108-116, vol. 81.

* cited by examiner

*Primary Examiner* — Susannah Chung
(74) *Attorney, Agent, or Firm* — Brinks Gilson & Lione

(57) ABSTRACT

The present invention relates to a method for producing 1-hydroxymethyl-1,2-diphenyloxiranes from 2,3-diphenylpropenals by means of epoxidation and reduction. The formation of objectionable by-products can be suppressed in that the reduction is started before the 2,3-5 diphenylpropenal is completely converted. The hydroxymethyl diphenyloxiranes represent valuable intermediate products for producing 1-azolylmethyl-1,2-diphenyloxiranes, wherein the latter can be easily produced from said intermediate products by introducing the azolyl group.

17 Claims, No Drawings

METHOD FOR PRODUCING HYDROXYMETHYL DIPHENYLOXIRANES AND CORRESPONDING 1-AZOLYLMETHYL-1,2-DIPHENYLOXIRANES

This application is a National Stage application of International Application No. PCT/EP2010/051380, filed Feb. 4, 2010, the entire contents of which is hereby incorporated herein by reference. This application also claims priority under 35 U.S.C. §119 to European Patent Application No. 09152176.5, filed Feb. 5, 2009, the entire contents of which is hereby incorporated herein by reference.

The present invention relates to a process for preparing 1-hydroxymethyl-1,2-diphenyloxiranes from 2,3-diphenylpropenals by epoxidation and reduction. The hydroxymethyldiphenyloxiranes are useful intermediates for the preparation of 1-azolylmethyl-1,2-diphenyloxiranes from which the latter can be prepared readily by introduction of the azolyl group. Accordingly, the invention also relates to a process for preparing 1-azolylmethyl-1,2-diphenyloxiranes.

The industrial importance of azolylmethyldiphenyloxiranes is enormous. In particular in the fields of pharmacy and crop protection, numerous active compounds from this structural class are encountered. Thus, for example, from the field of crop protection 1-(1,2,4-triazol-1-ylmethyl)-1,2-diphenyloxiranes such as epoxiconazole having fungicidal and in some cases also growth-regulating properties may be mentioned here.

Processes for preparing hydroxymethyldiphenyloxiranes are generally known, for example by epoxidation of diphenylpropenols using peroxides and specific catalysts (review: A. Pfenninger, "Asymmetric Epoxidation of Allylic Alcohols: The Sharpless Epoxidation", Synthesis 1986, 89). However, in general, the preferred diphenylpropenols which are substituted in the trans-position to the phenyl groups are difficult to obtain, if at all, or, on an industrial scale, the synthesis conditions can not be realized with reasonable expenditure.

It is known that hydroxymethyldiphenyloxiranes can be prepared in good yields by converting an appropriately substituted 2,3-diphenylpropenal by epoxidation into 1-formyl-1,2-diphenyloxirane, which is then reduced to give 1-hydroxymethyl-1,2-diphenyloxirane. Thus, EP 330 132, EP 332 073, EP 334 035, EP 352 673, EP 352 675 and EP 421 125 give examples of the epoxidation of substituted 2,3-diphenylpropenals, for example 2-(4-fluorophenyl)-3-(2-chlorophenyl)propenal, to the corresponding formyloxiranes and their subsequent reduction to the 1-hydroxymethyl-1,2-diphenyloxiranes.

However, during the epoxidation and reduction byproducts are formed. In particular when substituted 2,3-diphenylpropenals such as those required, for example, for preparing epoxiconazoles are used, a certain type of lipophilic byproduct which—in the case of the reaction mentioned above of 2-(4-fluorophenyl)-3-(2-chlorophenyl)propenal has the structure A

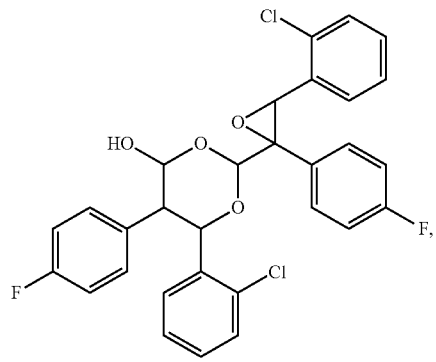

—is produced in significant amounts. It is particularly annoying that the byproduct is also found in the actual product of value, the azolylmethyldiphenyloxirane, if the contaminated hydroxymethyldiphenyloxirane is converted in the usual manner into the desired azolylmethyldiphenyloxirane. Since the byproduct has an adverse effect on the properties of the azolylmethyldiphenyloxirane, an expensive purification of the product of value is required.

Accordingly, it is an object of the present invention to provide a process for preparing hydroxymethyldiphenyloxiranes comprising reduced amounts of the lipophilic byproduct referred to at the outset. A content of less than 1% by weight, preferably of less than 0.6% by weight, based on the product of value is desirable.

The object is achieved by a process according to claim 1. Particular aspects of the process are subject matter of patent claims 2 to 5, 10 and 13 to 15.

Here, a 2,3-propenal of the formula (V):

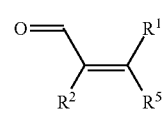

in which $R^1, R^2$
independently of one another are phenyl, where each phenyl radical independently of the other may have 1 to 3 substituents selected from the group consisting of halogen, cyano, nitro, $C_1$-$C_4$-alkyl, hydroxyl, $C_1$-$C_4$-alkoxy, halo-$C_1$-$C_4$-alkoxy, mercapto, $C_1$-$C_4$-alkylthio, halo-$C_1$-$C_4$-alkylthio, sulfinyl, sulfonyl, $C_1$-$C_4$-alkylsulfonyl, phenylsulfonyl, phenyl, phenoxy, amino, $C_1$-$C_4$-alkylamino, di-$C_1$-$C_3$-alkylamino, —NHCO—$C_1$-$C_3$-alkyl, —NHCOO—$C_1$-$C_4$-alkyl, —COO—$C_1$-$C_4$-alkyl and —CONH—$C_1$-$C_4$-alkyl, where each of the substituents phenyl, phenoxy and phenylsulfonyl independently of the others may have 1 to 3 substituents selected from the group consisting of halogen and $C_1$-$C_4$-alkyl; and $R^5$ is hydrogen or methyl, is epoxidized to give a formyloxirane of the formula (IV):

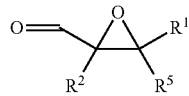

(IV)

in which $R^1$, $R^2$ and $R^5$ are as defined above, and the formyloxirane of the formula (IV) is reduced to give a hydroxymethyloxirane of the formula (III):

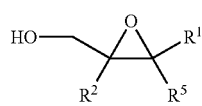

(III)

in which $R^1$, $R^2$ and $R^5$ are as defined above, the process being characterized in that the reduction is started while the amount of the compound of the formula (V) used in the reaction mixture is still at least about 2 mol %.

Accordingly, the process according to the invention is characterized in that the reduction is started before the 2,3-propenal of the formula (V) has been converted completely.

The resulting hydroxymethyloxirane of the formula (III) comprises substantially less of the lipophilic byproduct referred to at the outset. Preferably, the amount of byproduct is less than 1% by weight and in particular less than 0.6% by weight or 0.5% by weight. Such a result was unexpected.

There are, as described at the outset, numerous applications for the process according to the invention since the resulting hydroxymethyloxiranes are useful intermediates. Thus, the process according to the invention may also be part of a process according to claim 6, that is a process for preparing azolylmethyloxiranes of the formula (I):

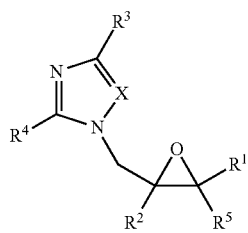

(I)

in which

X is N or CH;

$R^3$, $R^4$ independently of one another are hydrogen, halogen, $C_1$-$C_6$-alkyl, mercapto, —S—CN, $C_1$-$C_6$-alkylthio, $C_2$-$C_6$-alkenylthio, $C_6$-$C_{12}$-aryl-$C_1$-$C_3$-alkylthio or $C_6$-$C_{12}$-arylthio, where $C_2$-$C_6$-alkenylthio may have 1 to 3 substituents selected from the group consisting of halogen, $C_1$-$C_4$-alkyl and halo-$C_1$-$C_4$-alkyl, and the aryl in $C_6$-$C_{12}$-aryl-$C_1$-$C_3$-alkylthio may have 1 to 5 substituents selected from the group consisting of halogen, $C_1$-$C_4$-alkyl and halo-$C_1$-$C_4$-alkyl; and $R^1$, $R^2$ and $R^5$ have one of the meanings given here.

Particular aspects of the process are subject matter of patent claims 7 to 15.

As an additional step, such a process comprises the introduction of the azolyl group into the compound of the formula (III), where in general the hydroxyl group is replaced by a suitable nucleofugic group and then reacted with the desired azolyl compound.

The starting materials for the epoxidation reaction, i.e. the 2,3-diphenylpropenals of the formula (V), can be prepared in a manner known per se. For example, suitable phenylglyoxal O,O-acetals can be reacted with (a) dialkyl phenylphosphonates according to Horner, Wadsworth and Emmons (W. S. Wadsworth, Synthetic Applications of Phosphoryl-Stabilized Anions, Org. Reactions 25, 73 (1977)); (b) benzyltriphenylphosphonium halides according to Wittig (M. Ogata et al., Eur. J. Med. Chem. 24 (1989) 137); or (c) benzylmagnesium halides according to Grignard analogously to W. Madlung and M. E. Oberwegner, Chem. Ber. 65, 936 (1936). Furthermore available for preparing the 2,3-diphenylpropenals is, as variant d), the aldol condensation of arylalkylaldehydes with arylaldehydes according to WO 2005056498 A2, which affords 2,3-diphenylpropenals substituted in the cis-position to the phenyl groups, which propenals are readily epoxidized.

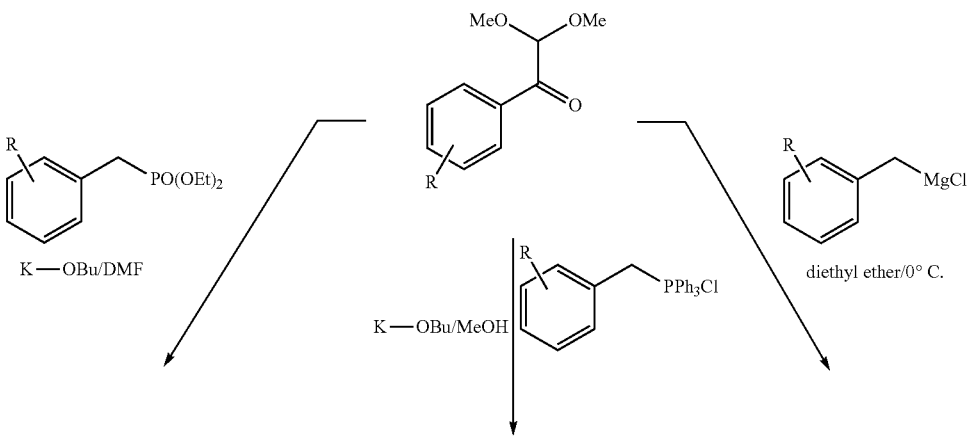

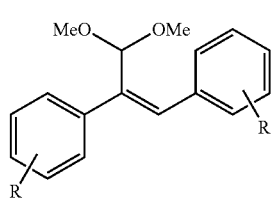 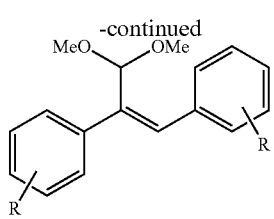 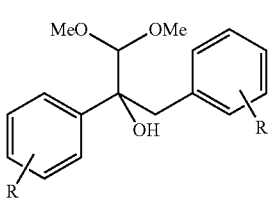

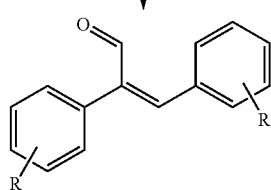 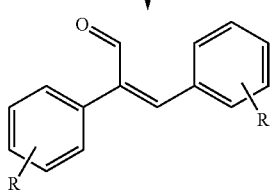 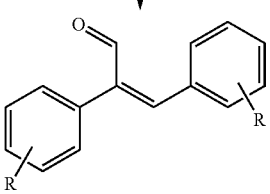

a) b) c)

d)

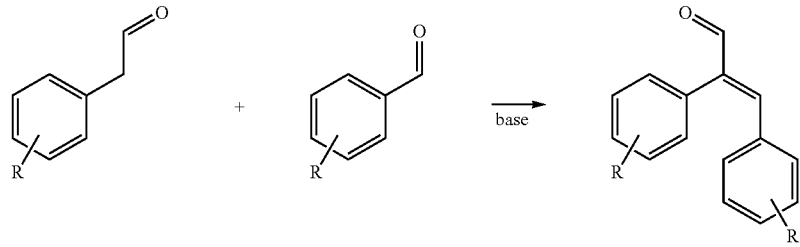

The epoxidation can be carried out in a manner known per se.

Customary oxidizing agents for the epoxidation include hydroperoxides, for example hydrogen peroxide, tert-butyl hydroperoxide, cumene hydroperoxide, tert-amyl hydroperoxide and trityl hydroperoxide, molecular oxygen, percarbonates, perborates and peroxycarboxylic acids, such as perbenzoic acid, meta-chloroperbenzoic acid, 4-nitroperbenzoic acid, monoperphthalic acid, peracetic acid, perpropionic acid, permaleic acid, monopersuccinic acid and trifluoroperacetic acid, and furthermore the salts, in particular the alkali metal or alkaline earth metal salts, of the percarboxylic acids, perboric acids and peracids, such as sodium percarbonate, sodium perborate or potassium peroxomonosulfate. Preference is given to sterically demanding hydroperoxides, such as tert-butyl hydroperoxide, which effect stereoselective formation of the preferred trans-oxiranes.

The oxidizing agent is generally employed in at least equimolar amounts and preferably in excess to the 2,3-propenal of the formula (V). The molar ratio of oxidizing agent to 2,3-propenal of the formula (V) is preferably from 3:1 to 1:1, particularly preferably from 2:1 to 1:1 and in particular from 1.5:1 to 1:1. Sterically demanding hydroperoxides such as tert-butyl hydroperoxide are preferably employed in a molar ratio of from 1.2:1 to 1:1.

The epoxidation is preferably carried out at a pH in the basic range, for example at a pH of from 7.1 to 14, preferably from 10 to 13. To adjust the desired pH, a suitable base is generally added to the reaction medium. Suitable bases are, for example, alkali metal and alkaline earth metal hydroxides, such as sodium hydroxide, potassium hydroxide, magnesium hydroxide or calcium hydroxide, alkali metal and alkaline earth metal carbonates, such as sodium carbonate, potassium carbonate, magnesium carbonate or calcium carbonate, and in particular alkali metal and alkaline earth metal bicarbonates, such as sodium bicarbonate, potassium bicarbonate, magnesium bicarbonate or calcium bicarbonate. Establishing the basic pH acts as a catalyst, and the added base is therefore also referred to as catalyst.

The base is employed in such an amount that the reaction medium has a pH of at least 7.1, for example from 7.1 to 14, preferably of at least 10, for example from 10 to 13. If hydrogen peroxide is used, the base is employed in such an amount that the hydrogen peroxide is preferably completely deprotonated (to $HOO^-$).

The epoxidation can be carried out in an aqueous or in a non-aqueous medium. Aqueous systems may be advantageous in particular when inorganic bases are used. When organic bases soluble in organic solvents are used, the epoxidation is preferably carried out in a non-aqueous medium. In this case, suitable organic solvents are solvents which are inert during the epoxidation reaction. Examples of suitable organic solvents are $C_1$-$C_4$-alkanols, such as methanol, ethanol, propanol, isopropanol and the butanols, cyclic and open-chain ethers, such as tetrahydrofuran, dioxane, diethyl ether, dipropyl ether, diisopropyl ether, dibutyl ether, tert-butyl methyl ether and the like, halogenated hydrocarbons, such as methylene chloride, chloroform or carbon tetrachloride, aromatic hydrocarbons, such as benzene, toluene, nitrobenzene, chlorobenzene, dichlorobenzene and the xylenes, carboxylic acid derivatives, such as dimethylformamide and ethyl acetate, nitriles, such as acetonitrile and propionitrile, and dimethyl sulfoxide.

The epoxidation is preferably carried out by initially charging the 2,3-diphenylpropenal of the formula (V) and adding the oxidizing agent and optionally the base. Here, the addition of the oxidizing agent and the base may take place either separately or else jointly, in one portion or preferably a little at a time. In particular, all of the base may be added first, and the oxidizing agent may then be added a little at a time.

During the epoxidation, the reaction temperature is generally from −20 to +80° C., preferably from −0 to 60° C. and in particular from 20° C. to 35° C.

According to the invention, the reaction product of the epoxidation is not isolated but, even while the epoxidation is still proceeding, the reaction mixture is subjected to the reduction. To this end, the progress of the epoxidation reaction may be monitored, for example by the conversion of starting material, i.e. the 2,3-diphenylpropenal of the formula (V).

According to the invention, to counteract against the formation of the lipophilic byproduct mentioned at the outset, the reduction is started while at least about 2, 3, 4 or 5 mol %, in particular cases at least about 7.5 mol % and under certain conditions at least about 10 mol % of the starting material initially introduced into the epoxidation reaction, i.e. of the 2,3-diphenylpropenal of the formula (V), are still present in the reaction mixture, i.e. have not yet reacted. On the other hand, in particular with a view to the possible formation of byproducts from the reduction of the diphenylpropenals and the concomitant loss of overall yield, it is expedient to start the reaction only once the epoxidation reaction has already proceeded to a certain degree. Thus, in general, the reduction can be started when more than about 80 mol %, preferably more than about 85 mol % and in particular more than about 90 mol % of the 2,3-diphenylpropenal of the formula (V) initially introduced into the epoxidation reaction have reacted, i.e. the amount of 2,3-diphenylpropenal in the reaction mixture is less than 20 mol %, preferably less than about 15 mol % and in particular less than about 10 mol % of the 2,3-diphenylpropenal of the formula (V) initially introduced into the epoxidation reaction. Taking into account the two contrary aims of achieving a most complete suppression of the byproduct A and achieving the highest total amount possible, it is particularly advantageous to carry out the reaction such that the reduction is started while about 2.5 mol % to 15 mol %, preferably about 3 mol % to 12 mol % and in particular about 5 mol % to 10 mol % of the starting material initially introduced into the epoxidation reaction, i.e. the 2,3-diphenylpropenal of the formula (V), are still present in the reaction mixture.

The amount of 2,3-diphenylpropenal in the reaction mixture can be determined in a manner known per se, for example by high pressure liquid chromatography (HPLC), which allows the progress of the reaction to be monitored at all stages.

The reduction can be carried out using, for example, complex hydrides or non-complex metal and semimetal hydrides. Complex hydrides are generally understood as meaning charged metal complexes comprising at least one hydride ligand. Examples of these are lithium aluminum hydride (LiAlH$_4$), LiAlH(O-tert-butyl)$_3$, LiAlH(O-methyl)$_3$, NaAlEt$_2$H$_2$, sodium borohydride (NaBH$_4$) and the like. Examples of non-complex metal and semimetal hydrides are boranes, such as BH$_3$, 9-BBN (9-borabicyclo[3.3.1]nonane) and disiamylborane, AlH$_3$, DIBAL-H (AlH(isobutyl)$_2$) and the like.

Preferred reducing agents are the abovementioned complex hydrides and non-complex metal and semimetal hydrides, and from among these particular preference is given to the alkali metal borohydrides, for example sodium borohydride.

In general, the reducing agent is employed in at least equimolar amounts and particularly preferably in excess to the 2,3-propenal of the formula (V). Preferably, the molar ratio of reducing agent to 2,3-propenal of the formula (V) is from 3:1 to 1:1, particularly preferably from 2:1 to 1:1 and in particular from 1.5:1 to 1:1.

The reduction is preferably carried out at a pH in the basic range, for example at a pH of from 7.1 to 14, preferably from 10 to 13. To establish the desired pH, a suitable base is generally added to the reaction medium. Suitable bases are, for example, alkali metal and alkaline earth metal hydroxides, such as sodium hydroxide, potassium hydroxide, magnesium hydroxide or calcium hydroxide, alkali metal and alkaline earth metal carbonates, such as sodium carbonate, potassium carbonate, magnesium carbonate or calcium carbonate, alkali metal salts of weak acids, such as borates, and organic bases, such as quaternary ammonium hydroxides and specific tertiary amines, such as diazabicyclooctane (DABCO), diazabicycloundecene (DBU), pentamethylguanidine or cyclic phosphorane bases, such as BEMP. Establishing the basic pH acts as a catalyst, and the added base is therefore also referred to as catalyst.

The base is employed in such an amount that the reaction medium has a pH of at least 7.1, for example from 7.1 to 14, preferably of at least 10, for example from 10 to 13. Here, however, attention has to be paid to the fact that concentrations of strong bases such as NaOH, KOH or quaternary ammonium hydroxides which are too high lead to increased formation of the byproduct described at the outset.

Since, according to the invention, the formyloxirane formed is not isolated, the reduction takes place in the reaction medium used for the epoxidation. However, it may be expedient to add further solvent before, during or after the addition of the reducing agent. This solvent may be a different solvent than that used for the epoxidation and may serve to dilute the reaction mixture and/or to establish conditions favorable for the formation and/or isolation of the hydroxymethyloxirane. Suitable solvents are, for example, aliphatic hydrocarbons, preferably those having 5 to 8 carbon atoms, such as pentane, cyclopentane, hexane, cyclohexane, heptane, octane or cyclooctane, or technical-grade alkane or cycloalkane mixtures, aromatic hydrocarbons, such as benzene, toluene and the xylenes, aliphatic acyclic and cyclic ethers having preferably 4 to 8 carbon atoms, such as diethyl ether, methyl tert-butyl ether, ethyl tert-butyl ether, dipropyl ether, diisopropyl ether, dibutyl ether, tetrahydrofuran or dioxane, or mixtures of the solvents mentioned above. Particular preference is given to using the ethers or aromatic hydrocarbons mentioned above.

The reaction is preferably carried out by optionally adding further solvent and adding the reducing agent and optionally the base. Here, the addition of the reducing agent and the base may take place either separately or else jointly, in one portion or preferably a little at a time. In particular, all of the base may be added first, and the reducing agent may then be added a little at a time.

During the reduction, the reaction temperature is generally from −20 to +80° C., preferably from −0 to 60° C. and in particular from 20° C. to 35° C.

The work-up of the reaction mixture from reduction reaction can be carried out in a customary manner, for example by deactivating unreacted reducing agent, for example by adding a protic solvent, such as water, or a C$_1$-C$_3$-alcohol, such as methanol, ethanol, propanol or isopropanol, to the reaction mixture, followed by purification, for example by extraction, chromatography and the like.

For reacting the hydroxymethyloxirane further, it is possible, inter alia by virtue of the high purity of the product, to use the solution of the hydroxymethyloxirane obtained after extraction and washing directly.

Thus, the preparation described at the outset of azolylmethyloxiranes of the formula (I) can be carried out, for example, by reacting a compound of the formula (II)

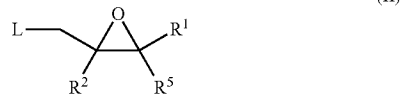

(II)

in which $R^1$, $R^2$ and $R^5$ are as defined herein and L is a nucleophilically substitutable leaving group,
with a compound of the formula (VI)

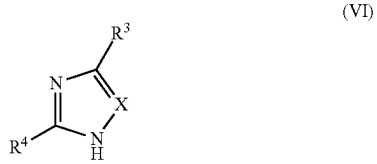

(VI)

in which $R^3$, $R^4$ and X are as defined herein,
or with a base addition salt of the compound of the formula (VI).

Further relevant details can be found, for example, in EP 0 352 675 A2, which is hereby incorporated herein in its entirety.

Accordingly, the reaction can be carried out in the presence of a base, a solvent or diluent and/or with addition of a reaction enhancer at temperatures between 10 and 120° C.

Suitable solvents and diluents include ketones, such as acetone, methyl ethyl ketone or cyclohexanone, nitriles, such as acetonitrile or propionitrile, alcohols, such as methanol, ethanol, isopropanol, n-butanol or glycol, esters, such as ethyl acetate, methyl acetate or butyl acetate, ethers, such as tetrahydrofuran, diethyl ether, dimethoxyethane, dioxane or diisopropyl ether, amides, such as dimethylformamide, dimethylacetamide or N-methylpyrrolidone, and furthermore dimethyl sulfoxide, sulfolane or appropriate mixtures.

Suitable bases which may optionally also be used as acid binders in the reaction, are, for example, alkali metal hydroxides, such as lithium hydroxide, sodium hydroxide or potassium hydroxide, alkali metal carbonates, such as sodium carbonate, potassium carbonate or cesium carbonate, or sodium bicarbonate, potassium bicarbonate or cesium bicarbonate, pyridine or 4-dimethylaminopyridine. However, it is also possible to use other customary bases.

Suitable reaction enhancers are, preferably, metal halides, such as sodium iodide or potassium iodide, quaternary ammonium salts, such as tetrabutylammonium chloride, tetrabutylammonium bromide, tetrabutylammonium iodide or tetrabutylammonium hydrogen sulfate, benzyltriethylammonium chloride or benzyltriethylammonium bromide, or crown ethers, such as 12-crown-4,15-crown-5,18-crown-6, dibenzo-18-crown-6 or dicyclohexano-18-crown-6.

The reaction is carried out, for example, at temperatures between 20 and 150° C., under atmospheric pressure or superatmospheric pressure, continuously or batch-wise.

If a base addition salt of the compound of the formula (VI) having a metal cation is used, it is expedient to carry out the reaction in the presence of a solvent or diluent and with addition of a strong inorganic or organic base at temperatures between −10 and 120° C. In this case, the preferred solvents and diluents include amides, such as dimethylformamide, diethylformamide, dimethylacetamide, diethylacetamide, N-methylpyrrolidone, hexamethylphosphoric triamide, sulfoxides, such as dimethyl sulfoxide, and finally sulfolane.

Suitable strong bases which may optionally also be used as acid binders in the reaction are, for example, alkali metal hydrides, such as lithium hydride, sodium hydride and potassium hydride, alkali metal amides, such as sodium amide and potassium amide, furthermore sodium tert-butoxide or potassium tert-butoxide, lithium triphenylmethyl, sodium triphenylmethyl or potassium triphenylmethyl and naphthalenelithium, naphthalenesodium or naphthalenepotassium.

Compounds of the formula (II) in which L is a nucleophilically substitutable leaving group such as halogen, $C_1$-$C_6$-alkyl-$SO_2$—O— or aryl-$SO_2$—O— can be obtained, for example, by converting the $CH_2OH$ group in compounds of the formula (III) into a suitable leaving group, for example into a group $CH_2L$ in which L has one of the given meanings. The conversion of alcohol functions in leaving groups is generally known and described, for example, in Organicum, VEB Deutscher Verlag der Wissenschaften, 17th edition, Berlin, 1988, page 179 ff, which is hereby incorporated herein in its entirety.

$C_1$-$C_6$-Alkyl is a straight-chain or branched alkyl radical having 1 to 6 carbon atoms. Examples are methyl, ethyl, n-propyl, isopropyl, n-butyl, 2-butyl, isobutyl or tert-butyl. $C_1$-$C_2$-Alkyl is methyl or ethyl, $C_1$-$C_3$-alkyl is additionally n-propyl or isopropyl.

Halo-$C_1$-$C_4$-alkyl is, for example, halomethyl, dihalomethyl, trihalomethyl, (R)-1-haloethyl, (S)-1-haloethyl, 2-haloethyl, 1,1-dihaloethyl, 2,2-dihaloethyl, 2,2,2-trihaloethyl, (R)-1-halopropyl, (S)-1-halopropyl, 2-halopropyl, 3-halopropyl, 1,1-dihalopropyl, 2,2-dihalopropyl, 3,3-dihalopropyl, 3,3,3-trihalopropyl, (R)-2-halo-1-methylethyl, (S)-2-halo-1-methylethyl, (R)-2,2-dihalo-1-methylethyl, (S)-2,2-dihalo-1-methylethyl, (R)-1,2-dihalo-1-methylethyl, (S)-1,2-dihalo-1-methylethyl, (R)-2,2,2-trihalo-1-methylethyl, (S)-2,2,2-trihalo-1-methylethyl, 2-halo-1-(halomethyl)ethyl, 1-(dihalomethyl)-2,2-dihaloethyl, (R)-1-halobutyl, (S)-1-halobutyl, 2-halobutyl, 3-halobutyl, 4-halobutyl, 1,1-dihalobutyl, 2,2-dihalobutyl, 3,3-dihalobutyl, 4,4-dihalobutyl or 4,4,4-trihalobutyl. This applies analogously to haloalkoxy and halo-alkylthio.

Hydroxy-$C_1$-$C_4$-alkyl is, for example, hydroxymethyl, (R)-1-hydroxyethyl, (S)-1-hydroxyethyl, 2-hydroxyethyl, (R)-1-hydroxypropyl, (S)-1-hydroxypropyl, 2-hydroxypropyl, 3-hydroxypropyl, (R)-2-hydroxy-1-methylethyl, (S)-2-hydroxy-1-methylethyl, 2-hydroxy-1-(hydroxymethyl)ethyl, (R)-1-hydroxybutyl, (S)-1-hydroxybutyl, 2-hydroxybutyl, 3-hydroxybutyl or 4-hydroxybutyl.

In the context of the present invention, halogen is fluorine, chlorine, bromine or iodine. Preferred substituents of a phenyl radical are fluorine and chlorine. This applies likewise to haloalkyl and haloalkoxy.

$C_2$-$C_6$-Alkenyl is a monounsaturated hydrocarbon radical having 2, 3, 4, 5 or 6 carbon atoms, for example vinyl, allyl (2-propen-1-yl), 1-propen-1-yl, 2-propen-2-yl or methallyl (2-methylprop-2-en-1-yl).

$C_6$-$C_{12}$-Aryl is a 6- to 12-membered, in particular 6- to 10-membered, aromatic cyclic radical. This includes, for example, phenyl and naphthyl.

The expression "substituted by 1 to 3 or 1 to 5 substituents selected from the group consisting of . . . " means "substituted by 1, 2 or 3 or 1, 2, 3, 4 or 5 substituents selected from the group consisting of . . . ", where the substituents may be identical or different.

Preferably, all of the radicals $R^x$ mentioned in the starting materials, intermediates and end products are stable toward the epoxidation and reduction conditions. However, if required, a labile radical may be protected temporarily by introducing suitable groups.

In the starting materials, intermediates and end products according to the invention, $R^1$ and $R^2$ are in particular phenyl having 1 to 3 substituents selected from the group consisting of halogen, nitro, $C_1$-$C_4$-alkyl, $C_1$-$C_4$-alkoxy, phenoxy, amino, halo-$C_1$-$C_2$-alkyl and phenylsulfonyl. Particular emphasis is given to end products and intermediates in which $R^1$ and $R^2$ independently of one another are phenyl having 1 to 3 halogen atoms. For example, $R^1$ is 4-fluorophenyl and $R^2$ is 2-chlorophenyl. Preferably, $R^1$ is 2-chlorophenyl and $R^2$ is 4-fluorophenyl (as in epoxiconazole) or $R^1$ is 2-chlorophenyl and $R^2$ is 2,4-difluorophenyl.

In the starting materials, intermediates and end products according to the invention, $R^3$ and $R^4$ are in particular hydrogen. According to a further particular embodiment, $R^3$ is in particular hydrogen and $R^4$ is in particular mercapto, —S—CN, $C_1$-$C_6$-alkylthio, $C_2$-$C_6$-alkenylthio (for example allylthio) or $C_6$-$C_{12}$-aryl-$C_1$-$C_3$-alkylthio (for example benzylthio), where $C_2$-$C_6$-alkenylthio (for example allylthio) may have 1 to 3 substituents selected from the group consisting of halogen, $C_1$-$C_4$-alkyl and halo-$C_1$-$C_4$-alkyl, and the aryl (for example phenyl) in $C_6$-$C_{12}$-aryl-$C_1$-$C_3$-alkylthio (for example benzylthio) may have 1 to 5 substituents selected from the group consisting of halogen, $C_1$-$C_4$-alkyl and halo-$C_1$-$C_4$-alkyl.

In the starting materials, intermediates and end products according to the invention, $R^5$ is in particular hydrogen.

According to a particular embodiment, the invention relates to a process for preparing [1,2,4]triazol-1-ylmethyloxiranes, i.e. X is a nitrogen atom.

The azolylmethyloxirane of the formula (I) is in particular a compound of the formula (Ia)

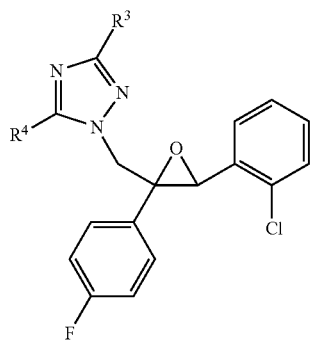

(Ia)

in which $R^3$ and $R^4$ are as defined herein and are preferably hydrogen.

According to a further particular embodiment, the azolylmethyloxirane of the formula (I) is a compound of the formula (Ib)

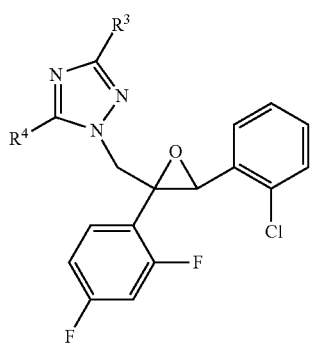

(Ib)

in which $R^3$ and $R^4$ are as defined herein and $R^5$ is preferably hydrogen and $R^4$ is preferably mercapto, —S—CN, $C_1$-$C_6$-alkylthio, $C_2$-$C_6$-alkenylthio (for example allylthio) or $C_6$-$C_{12}$-aryl-$C_1$-$C_3$-alkylthio (for example benzylthio), where $C_2$-$C_6$-alkenylthio (for example allylthio) may have 1 to 3 substituents selected from the group consisting of halogen, $C_1$-$C_4$-alkyl and halo-$C_1$-$C_4$-alkyl, and the aryl (for example phenyl) in $C_6$-$C_{12}$-aryl-$C_1$-$C_3$-alkylthio (for example benzylthio) may have 1 to 5 substituents selected from the group consisting of halogen, $C_1$-$C_4$-alkyl and halo-$C_1$-$C_4$-alkyl.

The starting materials, intermediates and end products of the present invention have one or more centers of asymmetry. Accordingly, they are obtained as optically active compounds, in most cases as mixtures of enantiomers. Thus, the racemate of the (2R,3S)- and (2S,3R)-enantiomers of the compound 1-[3-(2-chlorophenyl)-2-(4-fluorophenyl)oxiranyl]methyl-1H-[1,2,4]triazole is known under the common name "epoxiconazole". Thus, these and analogous compounds can be present in the form of 4 optically active enantiomers, 2 of which are to be referred to as cis-isomers and 2 as trans-isomers.

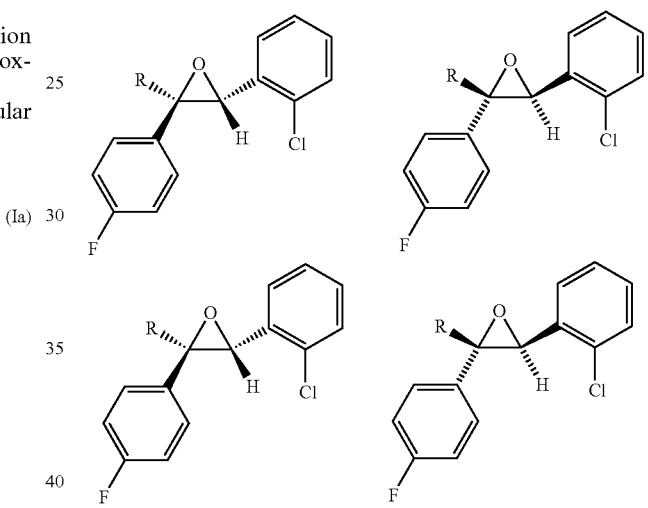

The process according to the invention comprises the preparation of all of these isomers, both as a mixture and in pure form. To this end, it may be required to choose the appropriate starting materials, to separate intermediates or end products and/or to select the reaction conditions such that the reaction proceeds with retention of the steric configuration. When carrying out the process according to the invention, it is also possible to bring about the formation of a particular steric configuration in a targeted manner, for example by enantioselective epoxidation.

The embodiments described below are intended to illustrate the invention in more detail without limiting it.

1. Preparation of 2,3-propenals of the Formula (V)
1.1 Reaction of Phenylglyoxal O,O-Acetals with Dialkyl Benzylphosphonates According to Horner and Emmons
1.1.1 Preparation of 2-(4-fluorophenyl)-3-(2-chlorophenyl)propenal At 40° C., 27.2 g (0.24 mol) of potassium tert-butoxide were added to 42.4 g (0.2 mol) of 4-fluorophenylglyoxal O,O-dimethyl acetal (96% pure) dissolved in 300 ml of dry dimethylformamide. Under a stream of nitrogen, the mixture was then heated to 100-110° C., and 58 g (0.22 mol) of diethyl (2-chlorobenzyl)-phosphonate were added dropwise over a period of 60 min. Stirring was continued for another 15-30 min, and during this time the mixture was checked by HPLC for complete conversion of the 4-fluorophenylglyoxal O,O-dimethylacetal. About 1000 ml of 10% strength sodium chloride solution were then added, and the mixture was extracted three times with 200 ml of methylene chloride. After washing and drying, the solvent was evaporated and 150 ml of MeOH and 20 ml of 16% strength hydrochloric acid were added to the residue. After about 30 min, the precipitation was brought to completion by further addition of water (20-30 ml), and the precipitate was filtered off with suction and washed acid-free using a mixture of methanol/water (3:1). Drying gave 48 g of 2-(4-fluorophenyl)-3-(2-chlorophenyl)propenal.

(Yield 91.7%, m.p. 87-89° C., 21% cis-isomer).

1.1.2 Preparation of 2-(phenyl)-3-(phenyl)propenal

Analogously to Example 1.1.1, phenylglyoxal O,O-dimethylacetal was reacted with diethyl benzylphosphonate (m.p. 90-92° C.).

1.1.3 Preparation of 2-(4-chlorophenyl)-3-(phenyl)propenal

Analogously to Example 1.1.1, 4-chlorophenylglyoxal O,O-dimethylacetal was reacted with diethyl benzylphosphonate (m.p. 82-84° C.).

1.1.4 Preparation of 2-(4-fluorophenyl)-3-(2-trifluoromethylphenyl)propenal

Analogously to Example 1.1.1, 4-fluorophenylglyoxal O,O-dimethylacetal was reacted with diethyl (2-trifluoromethylbenzyl)phosphonate. However, after the hydrolysis of the acetal, the product had to be worked up by distillation (b.p. at 0.25 mbar 112-114° C.).

1.2 Reaction of phenylglyoxal O,O-acetals with benzyltriphenylphosphonium halides According to Wittig

1.2.1 Preparation of 2-(4-fluorophenyl)-3-(2-chlorophenyl)propenal

At 5-10° C., 15.9 g of potassium tert-butoxide in 75 ml of dry methanol were introduced into a solution of 42.44 g (0.1 mol) of 2-chlorobenzyltriphenyl-phosphonium chloride in 200 ml of dry methanol, and after about 30 min 20.2 g (0.095 mol) of 4-fluorophenylglyoxal O,O-dimethylacetal (96% pure) in 25 ml of methanol were added. After 2 h under reflux at 65° C., the mixture was allowed to cool, the precipitated salt was filtered off and the solvent was removed from the mother liquor. The residue was then repeatedly digested with petroleum ether or methyl tert-butyl ether/cyclohexane (1:3) to remove the triphenylphosphine oxide, and the solution was once more concentrated by evaporation. Hydrolysis of the OO-acetal and the precipitation of the end product were carried out as described in Example 1.1. This gave 21.1 g of 2-(4-fluorophenyl)-3-(2-chlorophenyl)propenal.

(84.5% yield, m.p. 79-84° C., 56% cis-isomer).

1.3 Reaction of phenylglyoxal O,O-acetals with Benzylmagnesium Halides According to Grignard

1.3.1 Preparation of 2-(4-fluorophenyl)-3-(2-chlorophenyl)propenal

At 25-35° C., 5 g of 2-chlorobenzyl chloride and 0.2 ml of ethyl bromide were added over a period of a few minutes to 10.6 g (0.44 mol) of magnesium turnings in 20 ml of absolute ether. After the start of the reaction, a solution of 59.8 g (0.369 mol) of 2-chloro-benzyl chloride in 200 ml of absolute ether was added dropwise. The Grignard solution was then decanted off from excess magnesium and initially charged at 0° C. 71 g (0.35 mol) of 4-fluorophenylglyoxal O,O-dimethylacetal, dissolved in 400 ml of dry toluene, were then added dropwise such that the reaction temperature remained below 5° C., and the mixture was stirred until the acetal had been converted completely (HPLC) (about 2 h).

The mixture was then poured onto about 50 g of ice, and 16% strength hydrochloric acid was added such that the precipitate formed was just dissolved. The etherol phase was separated off, and the aqueous phase was extracted two more times with 100 ml of methyl tert-butyl ether. Following removal of the solvents on a rotary evaporator, the residue was treated in 300 ml of methanol and 40 ml of 16% strength hydrochloric acid, and the resulting precipitation was brought to completion using more water (about 50 ml). This gave 73 g of 2-(4-fluorophenyl)-3-(2-chlorophenyl)propenal. (69.7% yield, m.p. 82-85° C., 46% cis-isomer).

2. Preparation of Hydroxymethyloxiranes of the Formula (III)

2.1 Epoxidation and Reduction Carried Out Separately 125 g (0.479 mol) of 2-(4-fluorophenyl)-3-(2-chlorophenyl)propenal (DPP) from Example 1.1.1 were dissolved in 300 ml of methanol, and 2.7 ml (0.05 mol) of NaOH (48% strength) were added. Over a period of 120 min, 66 g (0.512 mol) of tert-BuOOH (70%) were then added dropwise such that the temperature remained at 31° C., and the mixture was then stirred for another 90 min to bring the epoxidation to completion (total reaction time=210 min, DPP conversion: 98.8%).

The mixture was then diluted with 100 ml of toluene, and 42.3 g of Borol solution (12.5% strength solution of $NaBH_4$ in 40% strength NaOH comprising 5.29 g of $NaBH_4$) were added. After work-up (1× extraction with 700 ml of toluene and 2× washing with 150 ml of water), a cis/trans mixture of the hydroxymethyloxirane in toluene with a yield of 92.2% trans-isomer was obtained.

The solid obtained contained 0.92% of byproduct A (Difox) and 0.09% of substituted 2-(4-fluorophenyl)-3-(2-chlorophenyl)propenol.

2.2 Epoxidation and Reduction Carried Out According to the Invention

2.2.1 165 Min Total Reaction Time, with 45 Min of Additional Stirring

The procedure of Example 2.1 was adopted; however, the total reaction time for the epoxidation was reduced to 165 min, with an additional stirring time of only 45 min. At a DPP conversion of 94.3%, the Borol solution was added, giving, after the reduction, a cis/trans mixture of the hydroxymethyloxirane in toluene with a yield of 92.4% trans-isomer.

The solid obtained contained 0.55% of byproduct A (Difox) and 0.55% of substituted 2-(4-fluorophenyl)-3-(2-chlorophenyl)propenol.

2.2.2 150 Min Total Reaction Time, with 30 Min of Additional Stirring

The procedure of Example 2.1 was adopted; however, the total reaction time for the epoxidation was reduced to 150 min, with an additional stirring time of only 30 min. At a DPP conversion of 94.3%, the Borol solution was added, giving, after the reduction, a cis/trans mixture of the hydroxymethyloxirane in toluene with a yield of 93.1% trans-isomer.

The solid obtained contained 0.24% of byproduct A (Difox) and 1.06% of substituted 2-(4-fluorophenyl)-3-(2-chlorophenyl)propenol.

2.2.3 120 Min Total Reaction Time without Additional Stirring

The procedure of Example 2.1 was adopted; however, the total reaction time for the epoxidation was reduced to 120 min, without any additional stirring. At a DPP conversion of 92.3%, the Borol solution was added, giving, after the reduction, a cis/trans mixture of the hydroxymethyloxirane in toluene with a yield of 91.6% trans-isomer.

The solid obtained contained 0.14% of byproduct A (Difox) and 1.29% of substituted 2-(4-fluorophenyl)-3-(2-chlorophenyl)propenol.

2.2.4 Cumene Hydroperoxide Instead of Tert-Butyl Hydroperoxide

The procedure of Example 2.2.2 was adopted; however, the tert-butyl hydroperoxide was replaced by cumene hydroperoxide. At a DPP conversion of 93.5%, the Borol solution was added, giving, after the reduction, a cis/trans mixture of the hydroxymethyloxirane in toluene with a yield of 92.1% trans-isomer.

The solid obtained contained 0.28% of byproduct A (Difox) and 0.98% of substituted 2-(4-fluorophenyl)-3-(2-chlorophenyl)propenol.

2.2.5 Higher Amount of Catalyst

The procedure of Example 2.1 was adopted; however the total reaction time for the epoxidation was reduced to 135 min, the mixture was stirred for an additional 30 min, the amount of catalyst was increased to 3.5 ml of 50% strength NaOH and the reaction ternperation after the start of the reaction was reduced from 31° C. to 25° C.

At a DPP conversion of 92.9%, the Borol solution was added, giving, after the reduction, a cis/trans mixture of the hydroxymethyloxirane in toluene with a yield of 90.1% trans-isomer.

The solid obtained contained 0.26% of byproduct A (Difox) and 1.34% of substituted 2-(4-fluorophenyl)-3-(2-chlorophenyl)propenol.

2.2.6 Reducing Agent in Two Portions

The procedure of Example 2.2.2 was adopted; however, for the reduction the Boral was, at a DPP conversion of 94.9%, added in two portions, i.e. 4.2 g immediately and the remainder (38.1 g) after 15 min. This gave a cis/trans mixture of the hydroxymethyloxirane in toluene with a yield of 92.1% trans-isomer.

The solid obtained contained 0.21% of byproduct A (Difox) and 0.64% of substituted 2-(4-fluorophenyl)-3-(2-chlorophenyl)propenol.

2.2.7 Tetramethylammonium Hydroxide Instead of NaOH

The procedure of Example 2.2.2 was adopted; however, the NaOH was replaced by 11.4 g (0.05 mol) of tetramethylammonium hydroxide (40%). At a DPP conversion of 92.2% at the addition of the Borol solution, a cis/trans mixture of the hydroxymethyloxirane in toluene with a yield of 88.9% trans-isomer was obtained.

The solid obtained contained 0.16% of byproduct A (Difox) and 1.14% of substituted 2-(4-fluorophenyl)-3-(2-chlorophenyl)propenol.

2.2.8 Comparative Example Analogously to Examples B and G from DE 3825586 (EP 352 675)

85 g (0.326 mol) of 2-(4-fluorophenyl)-3-(2-chlorophenyl)propenal (DPP) from Example 1.1.1 were dissolved in 300 ml of methanol, and 2.3 ml (0.043 mol) of NaOH (50% strength) were added. Over a period of 30 min, 27.7 g (0.794 mol) of $H_2O_2$ (50%) were then added dropwise such that the temperature remained at 30°, and stirring was then continued for another 6 h to bring the epoxidation to completion (reaction time=6.5 h, DPP conversion: >99.5%).

After the reduction with 35 g of Borol solution (12.5% strength solution of $NaBH_4$ in 40% strength NaOH) and following work-up (1× extraction with 600 ml of toluene and 2× washing with 150 ml of water), a cis/trans mixture of the hydroxymethyloxirane dissolved in toluene with a yield of trans-isomer of 63.5% was obtained.

The solid obtained contained 2.69% of byproduct A (Difox), 0.02% of substituted 2-(4-fluorophenyl)-3-(2-chlorophenyl)propenol and further byproducts (HPLC).

2.2.9 Further Comparative Example Analogously to Examples B and G from DE 3825586 (EP 352 675)

The procedure of Example 2.2.8 was adopted; however, the $H_2O_2$ was replaced by 45.3 g (0.352 mol) of tert-butyl hydroperoxide (70% in water). At a DPP conversion of 99.1%, a cis/trans mixture of the hydroxymethyloxirane in toluene with a yield of 82.2% trans-isomer was obtained.

The solid obtained contained 2.45% of byproduct A (Difox), 0.22% of substituted 2-(4-fluorophenyl)-3-(2-chlorophenyl)propenol and further byproducts (HPLC).

3. Preparation of Azolylmethyloxiranes of the Formula (I)

3.1 Triazolylmethyloxirane from Hydroxymethyloxirane According to the Invention 78 g (0.612 mol) of N,N-dimethylcyclohexylamine were added to the solution, obtained according to Example 2.2.2, of the cis/trans-hydroxymethyloxirane (130 g (0.471 mol) in 800 ml of toluene), and the mixture was dried by azeotropic distillation. At 25° C., 62 g (0.541 mol) of methanesulfonyl chloride were then added over a period of 1 h. After 30 min of additional stirring, the reaction had gone to completion and the salts formed were extracted using 2×200 ml of water. The toluene solution of the mesyloxymethyloxirane was evaporated under reduced pressure at temperatures below 80° C., and the residue was then taken up in 305 ml of dimethylformamide. This gave a solution of about 160 g (0.45 mol) of the mesyloxymethyloxirane in DMF which was initially charged and warmed to about 50° C. With vigorous stirring, 49 g (0.54 mol) of sodium 1,2,4-triazolide and 0.2 g of 1,2,4-triazole were added, and the mixture was then heated to 70° C. After 4 h of stirring at 70° C., complete conversion of the mesyloxymethyloxirane was checked by HPLC. When the mesyloxymethyloxirane content was <0.2%, 30 ml of methanol were added and the mixture was slowly cooled to 30° C. At the same time, 350 ml of water were added dropwise to precipitate the triazolylmethyloxirane formed. The precipitate obtained was filtered off with suction, washed 2× with a mixture of water/MeOH (80/20) and dried. This gave about 120 g of triazolylmethyloxirane of m.p. 134.7° C. which contained 96.2% trans-isomer, 2:7% sym-isomer, 0.37% cis-isomer and 0.20% byproduct A (Difox).

3.2 Imidazolylmethyloxirane from Hydroxymethyloxirane According to the Invention The procedure of Example 3.1 was adopted; however, the sodium 1,2,4-triazolide and 0.2 g of 1,2,4-triazole were replaced by 46.8 g (0.52 mol) of sodium imidazolide and 0.2 g of imidazole. This gave about 88 g of imidazolylmethyloxirane of m.p. 122-123° C., which contained 96.2% trans-isomer, 0.96% cis-isomer and 0.23% byproduct A (Difox).

3.3 Triazolylmethyloxirane from Impure Hydroxymethyloxirane

The procedure of Example 3.1 was adopted; however, the hydroxymethyloxirane from Example 2.2.2 was replaced by the hydroxymethyloxirane from Example 2.2.8. The triazolylmethyloxirane obtained contained 1.77% byproduct A (Difox) II. After recrystallization from cyclohexane, the content of II could be reduced to 0.39%.

The invention claimed is:

1. A process for preparing a compound of formula (III):

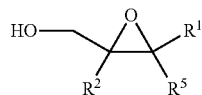
(III)

in which $R^1$, $R^2$
independently of one another are phenyl, where each phenyl radical independently of the other may have 1 to 3 substituents selected from the group consisting of halogen, cyano, nitro, $C_1$-$C_4$-alkyl, halo-$C_1$-$C_4$-alkyl, hydroxyl, $C_1$-$C_4$-alkoxy, halo-$C_1$-$C_4$-alkoxy, mercapto, $C_1$-$C_4$-alkylthio, halo-$C_1$-$C_4$-alkylthio, sulfinyl, sulfonyl, $C_1$-$C_4$-alkylsulfonyl, phenylsulfonyl, phenyl, phenoxy, amino, $C_1$-$C_4$-alkylamino, di-$C_1$-$C_3$-alkylamino, —NHCO—$C_1$-$C_3$-alkyl, —NH-COO—$C_1$-$C_4$-alkyl, —COO—$C_1$-$C_4$-alkyl and —CONH—$C_1$-$C_4$-alkyl, where each of the substituents phenyl, phenoxy and phenylsulfonyl independently of the others may have 1 to 3 substituents selected from the group consisting of halogen and $C_1$-$C_4$-alkyl; and $R^5$ is hydrogen or methyl, comprising expoxydizing a compound of formula (V):

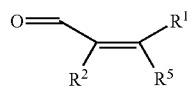
(V)

to give a compound of formula (IV):

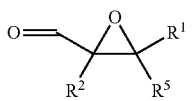
(IV)

and reducing the compound of formula (IV),
wherein the reduction reaction is started while the amount of the compound of the formula (V) used in the reaction mixture is still at least 2 mol %.

2. The process according to claim 1, where $R^1$ and $R^2$ independently of one another are phenyl having 1 to 3 halogen atoms.

3. The process according to claim 1, wherein said epoxydizing the compound of the formula (V) comprises reacting the compound of formula (V) with a hydroperoxide.

4. The process according to claim 2, where the hydroperoxide is selected from the group consisting of tert-butyl hydroperoxide, cumene hydroperoxide, tert-amyl hydroperoxide and trityl hydroperoxide.

5. The process according to claim 1, where the epoxidation reaction is carried out with base catalysis.

6. The process according to claim 1, wherein said reducing the compound of formula (IV) comprises adding an alkali metal borohydride and a base to the reaction mixture.

7. The process according to claim 5, where $R^1$ and $R^2$ independently of one another are phenyl having 1 to 3 halogen atoms.

8. A process for preparing a compound of formula (I):

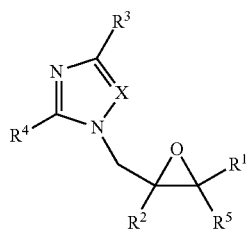
(I)

in which

X is N or CH;

$R^1$, $R^2$
independently of one another are phenyl, where each phenyl radical independently of the other may have 1 to 3 substituents selected from the group consisting of halogen, cyano, nitro, $C_1$-$C_4$-alkyl, halo-$C_1$-$C_4$-alkyl, hydroxyl, $C_1$-$C_4$-alkoxy, halo-$C_1$-$C_4$-alkoxy, mercapto, $C_1$-$C_4$-alkylthio, halo-$C_1$-$C_4$-alkylthio, sulfinyl, sulfonyl, $C_1$-$C_4$-alkylsulfonyl, phenylsulfonyl, phenyl, phenoxy, amino, $C_1$-$C_4$-alkylamino, di-$C_1$-$C_3$-alkylamino, —NHCO—$C_1$-$C_3$-alkyl, —NH-COO—$C_1$-$C_4$-alkyl, —COO—$C_1$-$C_4$-alkyl and —CONH—$C_1$-$C_4$-alkyl, where each of the substituents phenyl, phenoxy and phenylsulfonyl independently of the others may have 1 to 3 substituents selected from the group consisting of halogen and $C_1$-$C_4$-alkyl;

$R^3$, $R^4$
independently of one another are hydrogen, halogen, $C_1$-$C_6$-alkyl, mercapto, —S—CN, $C_1$-$C_6$-alkylthio, $C_2$-$C_6$-alkenylthio, $C_6$-$C_{12}$-aryl-$C_1$-$C_3$-alkylthio or $C_6$-$C_{12}$-arylthio, where $C_2$-$C_6$-alkenylthio may have 1 to 3 substituents selected from the group consisting of halogen, $C_1$-$C_4$-alkyl and halo-$C_1$-$C_4$-alkyl, and the aryl in $C_6$-$C_{12}$-aryl-$C_1$-$C_3$-alkylthio may have 1 to 5 substituents selected from the group consisting of halogen, $C_1$-$C_4$-alkyl and halo-$C_1$-$C_4$-alkyl; and $R^5$ is hydrogen or methyl, comprising epoxydizing a compound of formula (V):

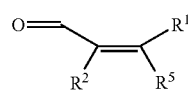
(V)

to give a compound of formula (IV):

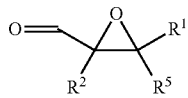
(IV)

reducing the compound of formula (IV) to give a compound of formula (III):

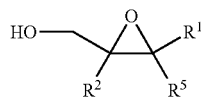
(III)

and introducing an azolyl group into the compound of the formula (III) to yield the compound of formula (I), wherein said reducing the compound of formula (IV) is started while the amount of the compound of the formula (V) in the reaction mixture is still at least 2 mol %.

9. The process according to claim 8, wherein said introducing the azolyl group into the formula (III) comprises reacting a compound of formula (II)

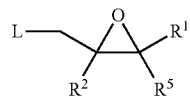

(II)

wherein L is a nucleophilically substitutable leaving group, with a compound of formula (VI), or a base addition salt thereof

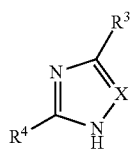

(VI)

10. The process according to claim 9, where L is halogen, $C_1$-$C_6$-alkyl-$SO_2$—O— or aryl-$SO_2$—O—.

11. The process according to claim 8, where X is N.

12. The process according to claim 11, where $R^1$ and $R^2$ independently of one another are phenyl having 1 to 3 halogen atoms.

13. The process according to claim 8, where the compound of formula (I) is the compound of the formula (Ia)

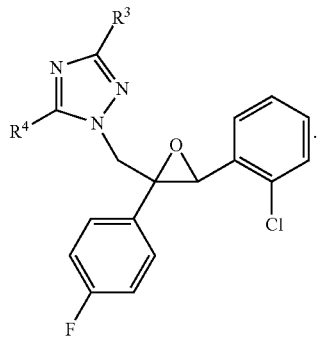

(Ia)

14. The process according to claim 13, where $R^3$ and $R^4$ are each hydrogen.

15. The process according to claim 1, where $R^5$ is hydrogen.

16. The process according to claim 1, where said reducing the compound of formula (IV) is started when the amount of the compound of the formula (V) in the reaction mixture is less than 20 mol %.

17. The process according to claim 1, where said reducing the compound of formula (IV) is started when the amount of the compound of the formula (V) in the reaction mixture is from 2.5 to 15 mol %.

* * * * *